(12) United States Patent
Diller et al.

(10) Patent No.: US 11,229,548 B2
(45) Date of Patent: Jan. 25, 2022

(54) THERMOREGULATORY MANIPULATION OF SYSTEMIC BLOOD PRESSURE

(71) Applicant: BOARD OF REGENTS, THE UNIVERSITY OF TEXAS SYSTEM, Austin, TX (US)

(72) Inventors: Kenneth R. Diller, Elgin, TX (US); Sepideh Khoshnevis, Austin, TX (US); Laura Hemmen, Lakeway, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 15/757,799

(22) PCT Filed: Sep. 9, 2016

(86) PCT No.: PCT/US2016/050988
§ 371 (c)(1),
(2) Date: Mar. 6, 2018

(87) PCT Pub. No.: WO2017/044775
PCT Pub. Date: Mar. 16, 2017

(65) Prior Publication Data
US 2018/0338857 A1 Nov. 29, 2018

Related U.S. Application Data

(60) Provisional application No. 62/216,735, filed on Sep. 10, 2015.

(51) Int. Cl.
| | |
|---|---|
| *A61F 7/08* | (2006.01) |
| *A47C 21/04* | (2006.01) |
| *A61F 7/00* | (2006.01) |
| *A61F 7/02* | (2006.01) |

(Continued)

(52) U.S. Cl.
CPC .............. *A61F 7/08* (2013.01); *A47C 21/042* (2013.01); *A47C 21/044* (2013.01);
(Continued)

(58) Field of Classification Search
CPC ................ A61F 7/08; A61F 2007/0054; A61F 2007/0059
See application file for complete search history.

(56) References Cited

U.S. PATENT DOCUMENTS

| | | |
|---|---|---|
| 7,996,936 B2 | 8/2011 | Marquette et al. |
| 8,603,150 B2 | 12/2013 | Kane et al. |

(Continued)

FOREIGN PATENT DOCUMENTS

WO 20130102051 A1 7/2013

OTHER PUBLICATIONS

Charkoudian, Nisha, Skin Blood Flow in Adult Human Thermoregulation: How It Works, When It Does Not, and Why, Mayo Clinic Ptoc. 2003; 78: 603-612 (Year: 2003).*

(Continued)

*Primary Examiner* — Kaitlyn E Smith
(74) *Attorney, Agent, or Firm* — Meunier Carlin & Curfman LLC (57) ABSTRACT

A system and/or method for proactively inducing a significant drop in blood pressure during sleep is provided herein. The system includes a blood pressure monitor and a stimulating device that provides stimulation to at least a portion of the person's body. For example, the stimulating device may stimulate a portion of the person's body corresponding to the person's peripheral thermoregulatory control tissue. The stimulation increases or maintains blood flow in the person's glabrous tissue. Additionally, the stimulating device provides stimulation in response to the person's blood pressure being above a predetermined threshold.

28 Claims, 10 Drawing Sheets

(51) Int. Cl.
    *A61B 5/021* (2006.01)
    *A61B 5/00* (2006.01)
    *A61B 17/00* (2006.01)

(52) U.S. Cl.
    CPC ............ *A47C 21/048* (2013.01); *A61B 5/021* (2013.01); *A61B 5/4836* (2013.01); *A61F 7/00* (2013.01); *A61F 7/0085* (2013.01); *A61F 7/02* (2013.01); *A61B 2017/00044* (2013.01); *A61B 2017/00075* (2013.01); *A61B 2017/00084* (2013.01); *A61F 2007/0002* (2013.01); *A61F 2007/0018* (2013.01); *A61F 2007/0029* (2013.01); *A61F 2007/0039* (2013.01); *A61F 2007/0045* (2013.01); *A61F 2007/0054* (2013.01); *A61F 2007/0056* (2013.01); *A61F 2007/0075* (2013.01); *A61F 2007/0076* (2013.01); *A61F 2007/0095* (2013.01)

(56) References Cited

U.S. PATENT DOCUMENTS

| | | | |
|---|---|---|---|
| 8,617,230 | B2 | 12/2013 | Diller et al. |
| 9,345,614 | B2* | 5/2016 | Schaefer ............... A61F 7/0085 |
| 9,717,623 | B2* | 8/2017 | Hyogo ...................... A61F 7/02 |
| 2001/0023364 | A1 | 9/2001 | Ahn et al. |
| 2008/0177350 | A1 | 7/2008 | Kieval et al. |
| 2013/0317578 | A1 | 11/2013 | Diller et al. |
| 2014/0358201 | A1* | 12/2014 | Scott ......................... A61F 7/12 607/105 |
| 2014/0364777 | A1 | 12/2014 | Swyer |
| 2015/0209175 | A1* | 7/2015 | Hyogo ...................... A61F 7/02 607/107 |
| 2016/0066701 | A1* | 3/2016 | Diller ................... A47C 21/044 5/423 |
| 2016/0374853 | A1* | 12/2016 | Grahn ...................... A61F 7/007 607/104 |
| 2017/0280883 | A1* | 10/2017 | Diller ...................... A61G 7/05 |

OTHER PUBLICATIONS

Cinar, Yildirim et al., Blood Viscosity and Blood Pressure: Role of Temperature and Hyperglycemia, American Journal of Hypertension, 2001; 14:433-438 (Year: 2001).*

Johnson, John et al., Cardiovascular adjustments to heat stress, Supplement 14. Handbook of Physiology, Environmental Physiology, Jan. 1, 2011 (Year: 2011).*

International Search Report and Written Opinion, dated Nov. 10, 2016, issued for International Application No. PCT/US2016/050988.

International Preliminary Report on Patentability, dated Mar. 22, 2018, issued for International Application No. PCT/US2016/050988.

Diller KR. 2015. Heat transfer in health and healing. J. Heat Trans. 137(10), 1030011-10300112.

Diller KR. 2015. Therapeutic recruitment of thermoregulation in humans by selective thermal stimulation along the spine. Adv. Heat Trans. 47, 341-396.

Hermida, et al., 2012, Blunted sleep-time relative blood pressure decline increases cardiovascular risk independent of blood pressure level—the "normotensive non-dipper" paradox, Chronobiol. Interntl. 30(1-2), 87-98.

Krauchi, et al., 1999, Warm feet promote the rapid onset of sleep, Nature 401, 36-37.

Krauchi K, 2007, The human sleep-wake cycle reconsidered from a thermoregulatory point of view, Physiol. Behavior 90, 236-245.

Taylor, et al., 2014. Hand and feet: physiological insulator, radiators and evaporators, Eur. J. Appl. Physiol. 114, 2037-2060.

Van Someren, E.J.W., 2000, More than a marker: interaction between the circadian regulation of temperature and sleep, age-related changes, and treatment possibilities, Chronobiol. Intl. 17(3), 313-354.

Weinert D, Waterhouse J, 2007, The circadian rhythm of core temperature: effects of physical activity and aging. Physiol. Behav. 90, 246-256.

* cited by examiner

THERMOREGULATORY MANIPULATION OF SYSTEMIC BLOOD PRESSURE

CROSS-REFERENCE TO RELATED APPLICATIONS

This application claims the benefit of U.S. Provisional Application No. 62/216,735, filed Sep. 10, 2015, the disclosure of which is incorporated herein by reference in its entirety.

GOVERNMENT SUPPORT

This invention was made with government support under Grant No. CBET1250659 awarded by the National Science Foundation. The government has certain rights in the invention.

BACKGROUND

Sleep is an important aspect of human health. In recent times, scientists have studied various aspects of sleep and found a variety of physiologic factors relating to sleep that may affect a person's health. For example, one such factor is blood pressure. A dip in blood pressure during sleep has been shown to improve cardiovascular health. In contrast, a blunted sleep-time decline in blood pressure (i.e., no dip in blood pressure) has been shown to increase the risk of cardiovascular disease. This risk is observed in both hypertensive and normotensive persons and is sometimes referred to as the "normotensive non-dipper paradox." The broad health consequences of a blunted sleep-time drop in blood pressure are enormous, correlating strongly with many manifestations of cardiovascular disease, including angina pectoris, myocardial infarction, cardiac arrest, sudden cardiac death, left ventricular hypertrophy, congestive heart failure, ischemic and hemorrhagic stroke, end stage renal failure, and diabetes.

Both sleep and body core temperature occur in coordinated circadian cycles, with core body temperature regulation playing a leading role in sleep induction and maintenance. For example, throughout the day a typical person will experience a relatively high body core temperature which peaks in the evening. As the body core temperature begins to drop, sleep onset occurs. The body core temperature continues to drop through the night. Prior to awakening in the morning, the process reverses and temperatures begin to rise, facilitating the completion of sleep. Much of the heat transfer that causes body core temperature changes occurs through glabrous skin, which in humans is skin that is naturally hairless, such as the skin found on the ventral portion of the fingers and toes, palmar surfaces of the hands, soles of feet, and other areas.

Some people do not experience a natural blood pressure dip during sleep, and consequently miss out on the associated health benefits. Others experience the dip inconsistently or to an extent that is not sufficient to provide health benefits. Therefore, a need exists for a system and/or method of proactively inducing a significant drop in blood pressure during sleep. A need further exists for inducing a blood pressure drop in a manner that promotes quality sleep—for example, by inducing the drop in conjunction with the sleep period of the circadian cycle. A system/method that meets these needs is described herein.

Other systems, methods, features and/or advantages will be or may become apparent to one with skill in the art upon examination of the following drawings and detailed description. It is intended that all such additional systems, methods, features and/or advantages be included within this description and be protected by the accompanying claims.

BRIEF SUMMARY

According to various implementations, a system for modifying a person's blood pressure includes a stimulating device to provide stimulation to at least a portion of the person's body. The stimulation increases or maintains blood flow in the person's glabrous tissue. In some implementations, the system further includes a blood pressure monitor to monitor a blood pressure of the person, and the stimulating device provides the stimulation in response to the person's blood pressure being above a predetermined threshold.

In some implementations, the portion of the person's body to which the stimulation is provided corresponds to the person's peripheral thermoregulatory control tissue (e.g., a cervical spinal region of the person or a lumbar spinal region of the person).

In some implementations, the stimulating device provides heating to the person's body such that the person's arterio-venous anastomoses (AVAs) are vasodilated. For example, in some implementations, the heating is applied to the persons' peripheral thermoregulatory control tissue. However, in some implementations, the stimulating device provides cooling to the person's body such that the person's physiological temperature remains constant or is lowered.

In some implementations, the stimulation includes warming sufficient to lower the blood pressure of the user.

In some implementations, the stimulating device modulates stimulation levels based on feedback from the blood pressure monitor.

In some implementations, the stimulating device is a climate-controlled bed. In some implementations, the climate-controlled bed comprises at least one climate zone. In addition, the climate-controlled bed may also include a thermoelectric device that transfers thermal energy between the thermoelectric device and the climate zone of the climate-controlled bed. In some implementations, the thermoelectric device includes an energy source, one or more conduits, and a fluid flowing through the conduits to transfer thermal energy between the energy source and the climate zone of the climate-controlled bed. For example, one or more conduits include at least one warming duct and at least one cooling duct, and the climate zones include a warming zone and a cooling zone. The warming duct delivers warm air to the warming zone, and the cooling duct delivers cool air to the cooling zone.

In some implementations, the climate-controlled bed includes a thermoelectric sourced cooler and at least one conduit between the thermoelectric sourced cooler and the climate zone. Fluid flowing through the conduit transfers a cooling effect to the climate zone from the thermoelectric sourced cooler.

In some implementations, the climate-controlled bed includes an electric sourced heater and at least one conduit between the electric sourced heater and the climate zone. Fluid flowing through the conduit transfers heat to the climate zone from the electric sourced heater.

In some implementations, the stimulating device provides the stimulation corresponding to the onset of sleep.

Various other implementations include a method for modifying a person's blood pressure. The method includes: (1) determining a first blood pressure of the person; and (2)

applying a warming stimulus to a portion of the person's body sufficient to lower the person's blood pressure.

In some implementations, the warming stimulus causes the person's arteriovenous anastomoses (AVAs) to vasodilate.

In some implementations, the portion of the person's body corresponds to the person's peripheral thermoregulatory control tissue (e.g., a cervical spinal region of the person or a lumbar spinal region of the person).

In some implementations, the method further comprises determining a second blood pressure of the person and adjusting the warming stimulus based on the second blood pressure determination. The application of the warming stimulus corresponds to the onset of sleep, in some implementations.

In some implementations, the method further includes applying a cooling stimulus to the person's body such that the person's physiological temperature remains constant or is lowered.

BRIEF DESCRIPTION OF THE DRAWINGS

The following detailed description will be better understood when read in conjunction with the appended drawings, in which there is shown one or more of the multiple embodiments of the present invention. It should be understood, however, that the various embodiments of the present invention are not limited to the precise arrangements and instrumentalities shown in the drawings.

DETAILED DESCRIPTION

Modulation of blood flow to arteriovenous anastomoses ("AVAs") in glabrous skin of the hands and feet—commonly referred to as "distal blood flow"—plays a major role in modulating blood pressure. The AVAs in glabrous skin function as the primary heat transfer portals between the body core and the environment. Vasodilated AVAs can have diameters ten or more times greater than do the parallel capillaries, acting as flow shunts in the vascular network. As a consequence, when the AVAs are vasodilated the heart will be pumping against a lower resistance and will require less pumping pressure to maintain blood flow. Since the AVAs vasodilate in conjunction with the circadian sleep pattern, the blood pressure undergoes a dip that is associated with increased cardiovascular health. Similarly, when the AVAs vasoconstrict, blood pressure rises.

In order to accomplish increased glabrous skin blood flow and an accompanying drop in blood pressure, selective thermal stimulation is utilized. For example, the selective thermal stimulation may be applied to the peripheral thermoregulatory control tissue, i.e. control tissue peripheral to the preoptic anterior hypothalamus thermoregulatory control center in the brain. The peripheral thermoregulatory control tissue can include, for example, the cervical spinal region and/or lumbar spinal region of a person.

A system and/or method for proactively inducing a significant drop in blood pressure during sleep is provided herein. The system includes a stimulating device that provides stimulation to at least a portion of the person's body. For example, the stimulating device may stimulate a portion of the person's body corresponding to the person's peripheral thermoregulatory control tissue. The stimulation increases or maintains blood flow in the person's glabrous tissue. Additionally, the stimulating device provides stimulation in response to the person's blood pressure being above a predetermined threshold. A blood pressure monitor may be used to record the blood pressure, although it may not be not necessary to achieve the desired physiological outcome.

Figure 1:
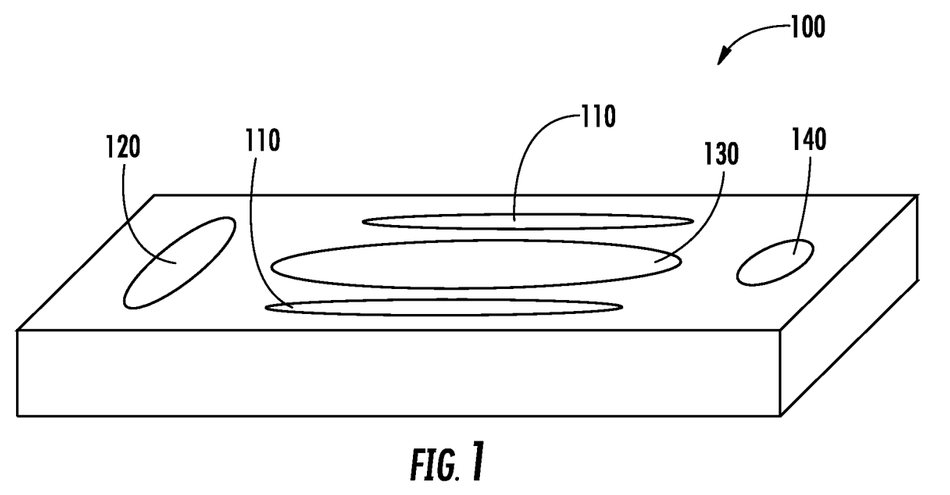
FIG. 1 is an example embodiment of a climate-controlled bed having multiple climate zones.

FIG. 1 shows an example embodiment of a climate-controlled bed. Bed 100 is shown as having a plurality of climate zones. For example, side climate zones 110 are located along the sides of bed 100. Foot climate zone 120 is located toward the foot end of bed 100. Central climate zone 130 is located in the center of bed 100. Finally, upper climate zone 140 is located near the head of the bed. In one example embodiment, side climate zones 110, foot climate zone 120, and upper climate zone 140 are used as warming zones. In this example embodiment, central climate zone 130 may be used as a warming or cooling zone depending on the sleeper's temperature and blood flow. In some embodiments, upper climate zone 140 is provided in the form of a pillow. A pillow may be useful in warming the cervical spinal area of a person because a pillow conforms to the head and neck better than the surface of a bed. Additionally, upper climate zone 140 may extend down to at least the person's lumbar spinal region.

In an example embodiment, a zone may be warmed or cooled via a thermoelectric energy source to provide warming or cooling to these zones. Warming or cooling may be provided in any number of ways, including for example via air flow, other types of fluid flow, or electrical resistance. The thermoelectric energy source may be used to simultaneously provide warming and cooling capacity to different zones. Alternatively, a plurality of thermoelectric energy sources may be implemented in order to have a dedicated energy source for warming and cooling, respectively.

Figure 2:
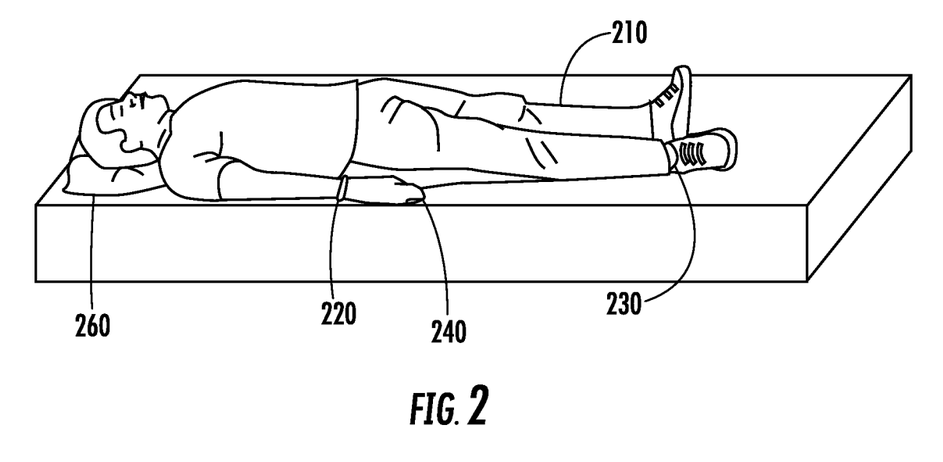
FIG. 2 is an example embodiment of a sleeper in a sleeping position.

Monitoring the user may be done in a variety of ways. FIG. 2 shows an example embodiment of a user 210 in a sleeping position. The user is depicted as being fully clothed, but of course user 210 is likely to be dressed in appropriate sleep attire. In an example embodiment, user 210 is wearing a first sensor 220. First sensor 220 is shown as being attached to the arm of user 210, however the sensor may be placed in any other suitable location. Sensor 220 may measure a variety of physiological properties, including for example temperature, heart rate, blood pressure, and/or motion. Sensor 220 may be incorporated into a device such as a wrist band, forearm band, or the like.

FIG. 2 discloses additional sensors as well. For example, a second sensor 230 is shown attached to the user near the ankle. Second sensor 230 may be placed on the calf or ankle such that it contacts non-glabrous skin and provides a temperature measurement for that type of skin. An additional sensor may be located on glabrous skin in order to provide a temperature comparison between the user's glabrous and non-glabrous skin, which may be interpreted as an indication of the level of blood flow to glabrous skin and of the status of the thermoregulatory function, especially in relation to the circadian cycle. For example, third sensor 240 may be placed on the hands or feet to measure the temperature of the glabrous skin at those locations. Additionally, a finger clip pulse oximeter may be incorporated into, for example, third sensor 240 for use on the user's finger and may be in conjunction with several electrical sensors on the chest skin surface. Additional sensors may be incorporated at other locations of the user's body. The various sensors may be used to determine at least temperature, mean arterial pressure, and glabrous blood flow.

Figure 3:
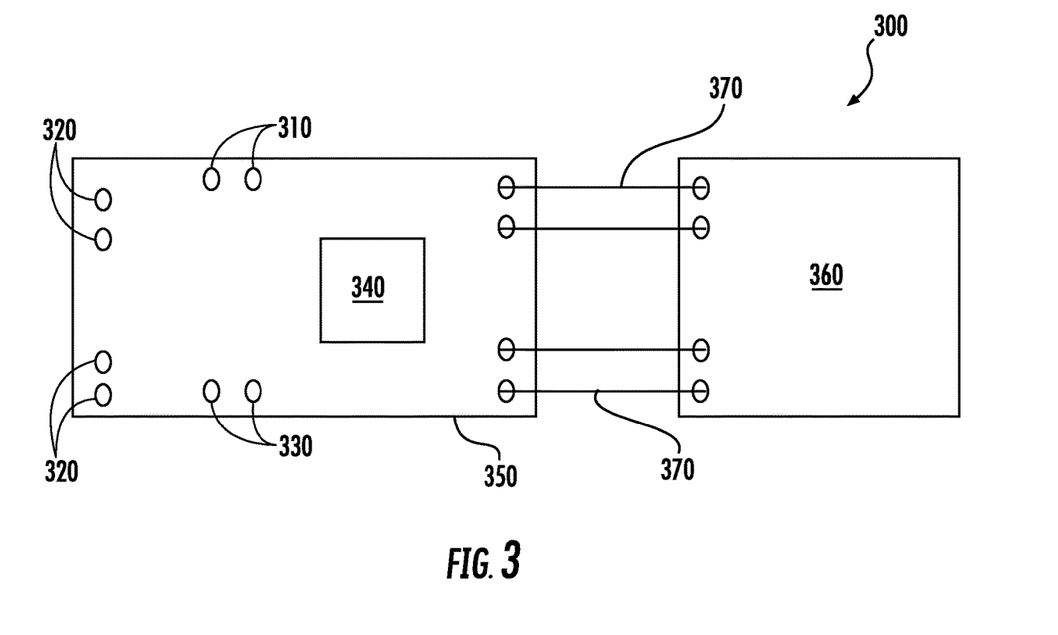
FIG. 3 is an example embodiment of a control system.

The various sensors described above can be connected directly or wirelessly to a control system. FIG. 3 discloses control system 300, which can include controller 350 and thermoelectric controller 360. In an example embodiment, control system 300 is responsible for receiving inputs from all available sensors, determining which zones to heat/cool, and instructing the thermoelectric energy source to perform particular heating and/or cooling actions. In the example embodiment of FIG. 3, controller 350 receives power inputs 310, temperature inputs 320, and non-temperature physiological inputs 330. Power inputs 310 may include, for example, a connector that plugs into a power outlet near the bed. Temperature inputs 320 include any temperature sensors on glabrous and/or non-glabrous skin of the user. Non-temperature physiological inputs 330 may include measurements of heart rate, blood pressure, oxygen levels, and so on. Other physiological inputs may be incorporated into the design as well. The particular number of input ports shown in FIG. 3 is not intended to be limiting—any number of sensors may be used.

In an example embodiment, controller 350 receives various inputs and determines, via a logic processor 340, how to heat and/or cool various zones of bed 100. For example, logic processor 340 may be capable of determining sleep onset based on information gathered from the user using predetermined sleep factors. Predetermined sleep factors include any factor relevant to the user's sleep. Examples include the circadian cycle of temperature variation, the time of day or night, the user's temperature on glabrous or non-glabrous skin sites, the user's heart rate, blood pressure, or blood oxygen levels, and so on. Logic processor 340 can be equipped with data regarding the natural circadian cycle of temperature variation. Using that data and comparing it to the data measured from the user, logic processor 340 can determine the appropriate method of facilitating sleep for the user. In other embodiments, logic processor 340 monitors blood pressure and determines whether the user's blood pressure should be modified.

For example, if the blood pressure is above a particular threshold, logic processor 340 may determine that a modification in blood pressure is needed. After making that determination, logic processor 340 causes controller 350 to communicate instructions to thermoelectric controller 360 via an electrical interface 370. Thermoelectric controller 360 is capable of relaying instructions to a thermoelectric device itself, which includes the thermoelectric energy source and provides heating and/or cooling as desired. For example, thermoelectric controller 360 may provide warming to the user's peripheral thermoregulatory control tissue, causing the user's AVAs to vasodilate as well as a corresponding dip in blood pressure. The controller 350 may also be equipped with a data logging or recording function to retain information about a sleeper during sleep and may be recovered at a later time for analysis. After providing the prescribed heating or cooling, logic process 340 can receive updated information from the various sensors to determine whether the goal (e.g., lowering blood pressure below a certain threshold) was accomplished. Based on this determination, the logic processor 340 can decide whether to continue heating, cease heating, increase heating, and so on.

Figure 4:
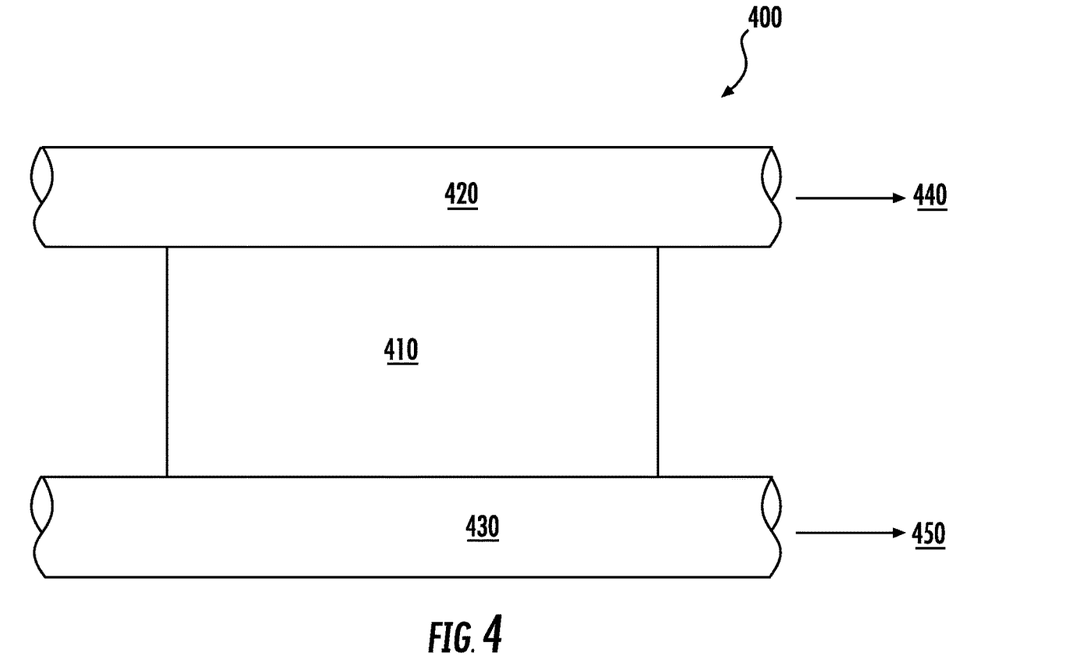
FIG. 4 is an example embodiment of a thermoelectric energy source providing cooling and/or warming air.

FIG. 4 discloses a thermoelectric device 400 for use in the example embodiments described above, as well as other embodiments. Thermoelectric device 400 is capable of providing warming and/or cooling capacity to different areas of the bed. In an example embodiment, thermoelectric device 400 includes an energy source 410. Energy source 410 may use, for example, electrical energy in order to heat or cool a fluid. While FIG. 4 shows energy source 410 as a single device that provides both heating and cooling services, it may alternatively comprise two separate devices that are responsible for heating and cooling, respectively. In one embodiment, energy source 410 uses heat created by cooling a fluid in conjunction with the cooled fluid to simultaneously warm and cool different locations of the bed. In another implementation, the energy source 410 may be an electric heater that provides thermal energy to a fluid for heating a climate zone. And, in other implementations, the energy source 410 may be a thermoelectric sourced cooler, such as but not limited to the LENX TEC2, for cooling the climate zone. In some implementations, the energy source 410 uses the Peltier effect to achieve cooling.

In an example embodiment, energy source 410 can be operatively connected to conduits that carry heated or cooled fluid to various areas of the bed. In the embodiment of FIG. 4, a cold-side air duct 420 and a warm-side air duct 430 is depicted. The cold-side air duct 420 is attached to energy source 410 such that a cooling air flow 440 is directed through cold-side air duct 420. Cooling air flow 440 may be directed to multiple different zones of the bed depending on the needs of the user. The warm-side air duct 430 is attached to energy source 410 such that a warming air flow 450 is directed through warm-side air duct 430. Warming air flow 450 may be directed to multiple different zones of the bed depending on the needs of the user. Cooling air flow 440 and warming air flow 450 may be sent to different areas of the bed simultaneously.

Although FIG. 4 is discussed in terms of warming and cooling air flow, other types of fluid can be substituted for air. For example, in one embodiment warming water is provided at about 40-45 degrees Celsius, while cooling water is provided at about 20 degree Celsius. The flow rate, contact surface area, and bodily contact location may vary the temperature of the fluid used.

Figure 5:
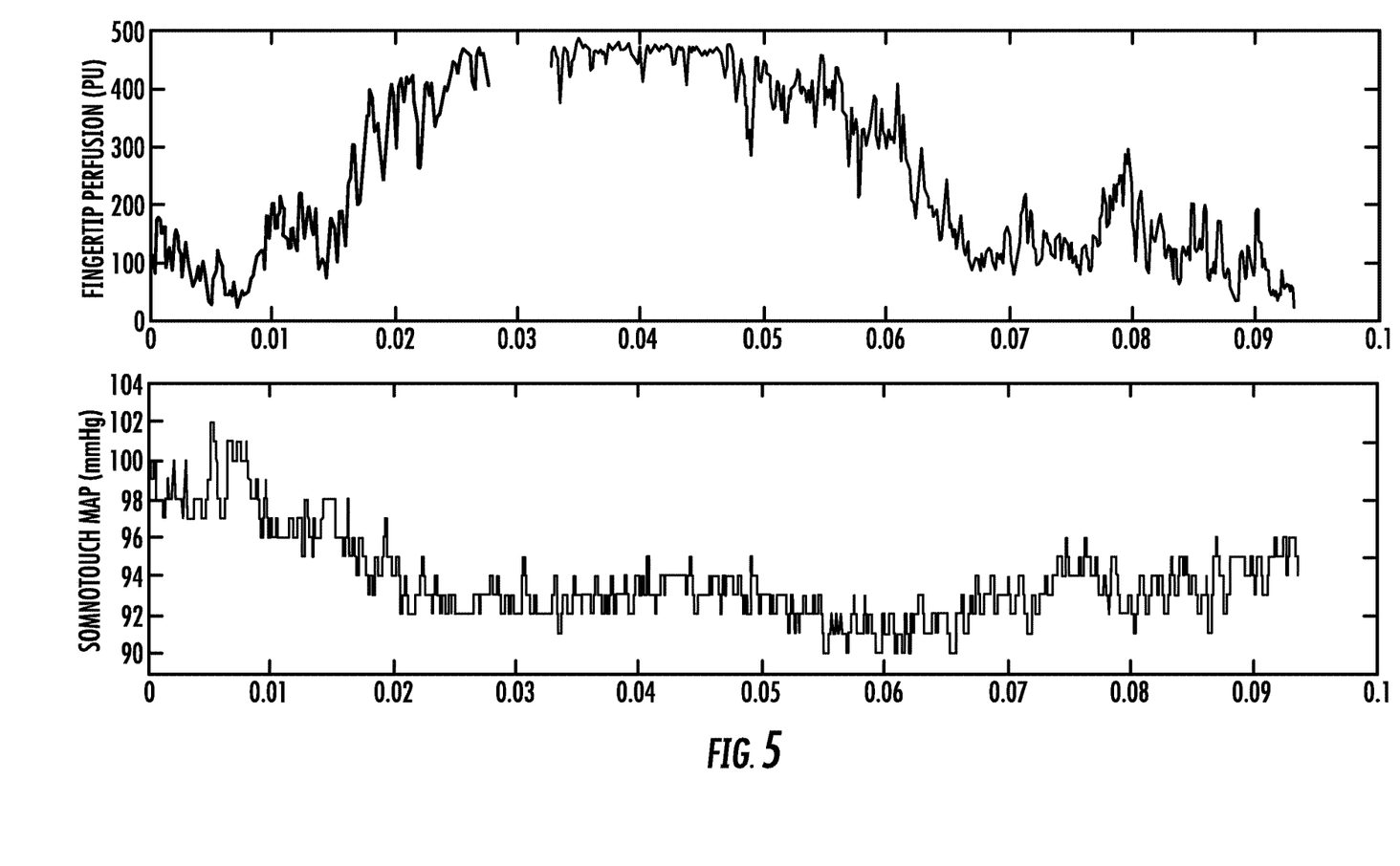
FIG. 5 is a pair of graphs showing data reflecting fingertip perfusion and mean arterial pressure over time in a subject.

FIG. 5 is a pair of graphs showing data reflecting fingertip perfusion and mean arterial pressure over time in a subject. The x-axis in each graph is time, shown as a fraction of a 24-hour day. In each graph the first 18 minutes (or 0.0-0.0125) represent a baseline condition of the person being measured. That is, no external heating or cooling was applied to the person during this period of time. In FIG. 5, heating was applied to the person's thermoregulatory control tissue starting at about the 0.0125 mark and tapering off between 0.05 and 0.07. In response to the heat applied to the thermoregulatory control tissue, the person's glabrous blood flow (measured as fingertip perfusion) visibly increased and remained elevated until the heat was removed and the person returned to a more natural baseline state (after 0.07). In conjunction with the rising glabrous blood flow, the person's blood pressure (measured as mean arterial pressure) visibly dropped from the baseline state. Notably, the person's blood pressure remained lower than the baseline state even after their glabrous blood flow rate returned to the baseline levels.

Figure 6:
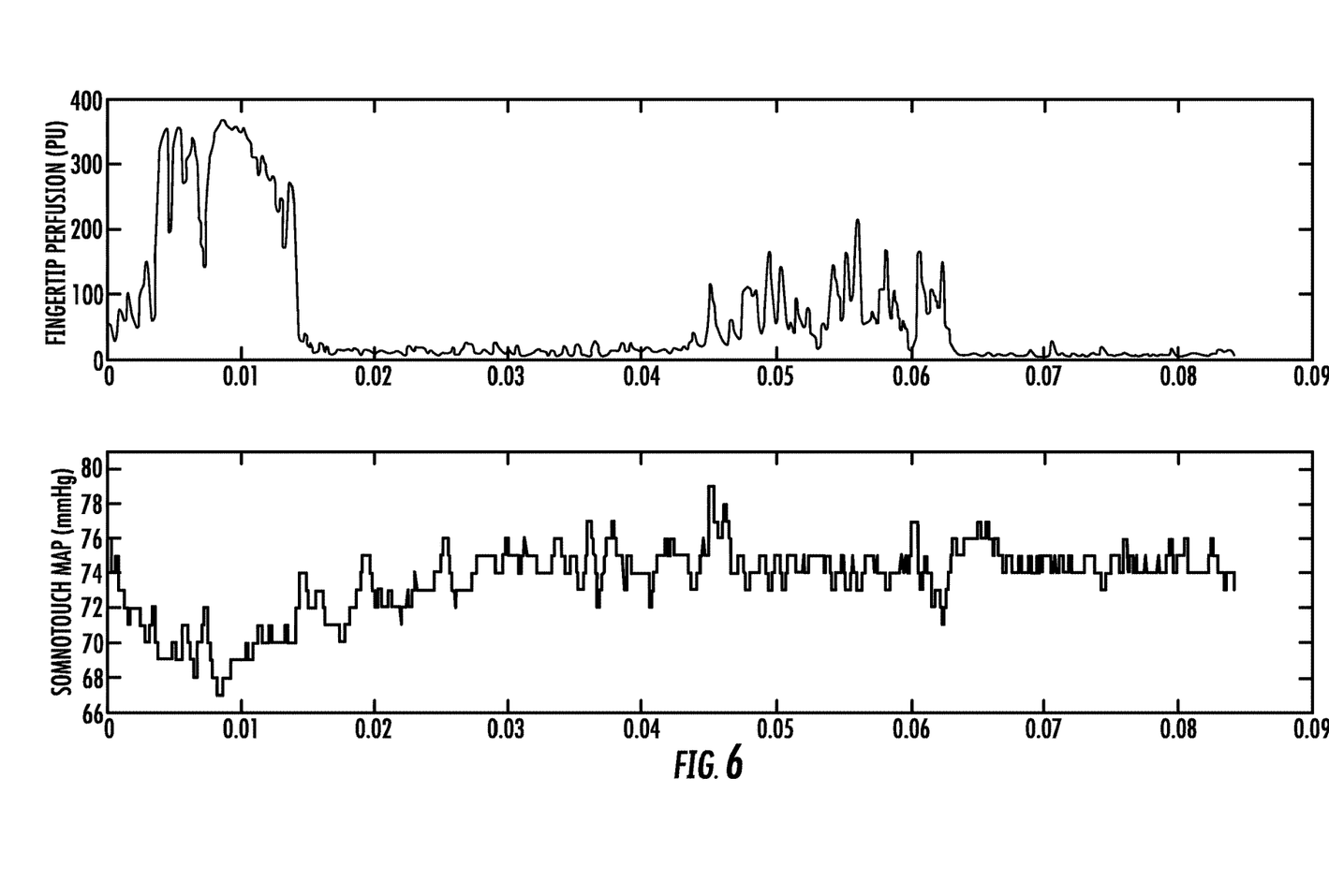
FIG. 6 is a pair of graphs showing data reflecting fingertip perfusion and mean arterial pressure over time in a subject.

FIG. 6 is a pair of graphs with similar measurements as those in FIG. 5. Again, the first 18 minutes (0.0-0.0125) represent a baseline during which no heating or cooling was applied to the person. The person tested in FIG. 6 shows a fluctuating, but generally high, glabrous blood flow rate in their baseline state. They also show a relatively low blood pressure baseline. Cooling was applied after the 0.0125 mark, dropping the person's glabrous blood flow rate quickly down to almost zero. This drop in blood flow corresponds with a corresponding rise in blood pressure over time. When the cooling was removed at around the 0.045 mark, the person's glabrous blood flow rate began to fluctuate without rising much. Additional cooling at about the 0.0625 mark lowered the glabrous blood flow rate again. During these portions of the test, the person's blood pressure remained high, correlating clearly with the glabrous blood flow rate.

Figure 7:
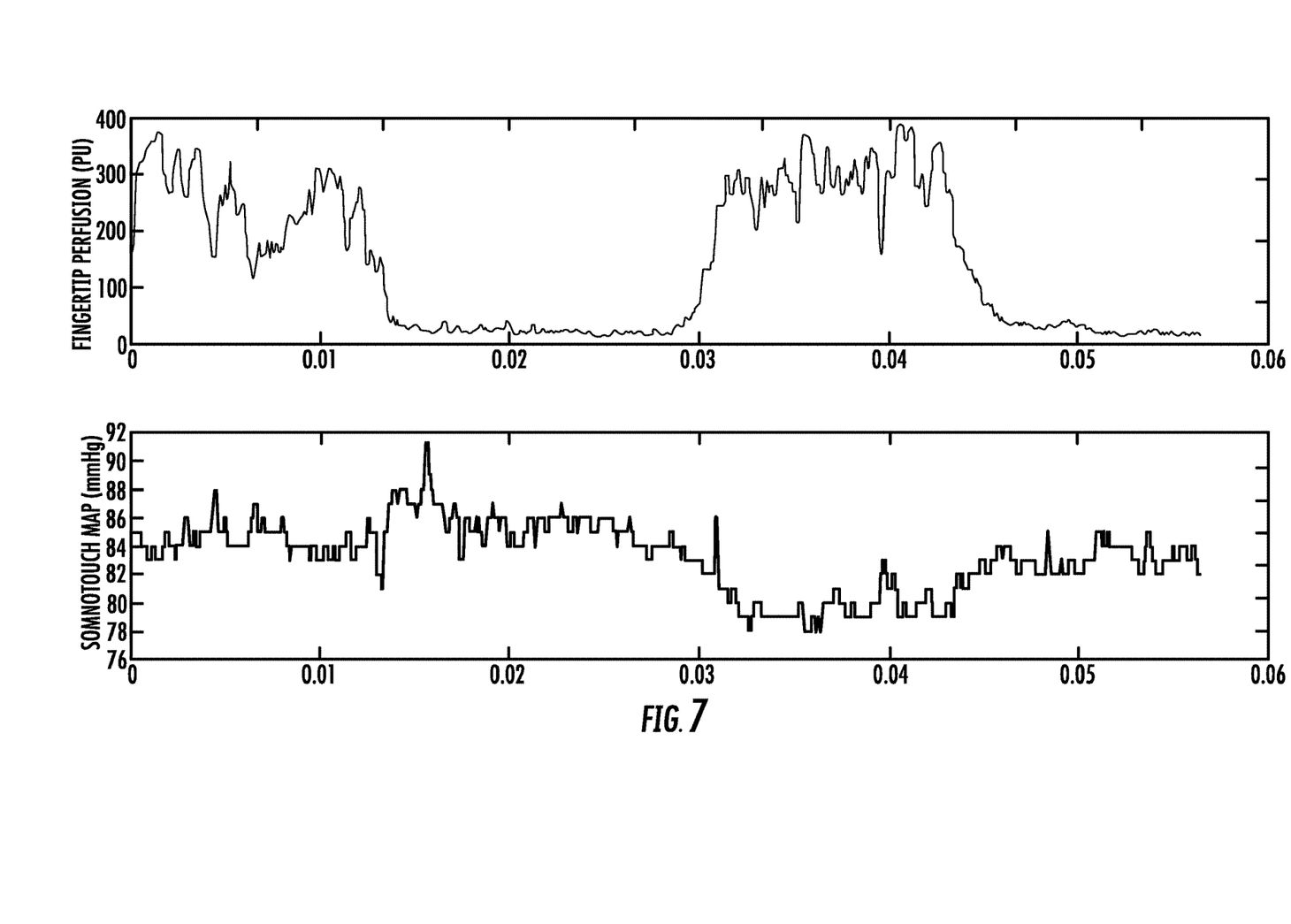
FIG. 7 is a pair of graphs showing data reflecting fingertip perfusion and mean arterial pressure over time in a subject.

FIG. 7 is a pair of graphs with similar measurements as those in FIGS. 5 and 6. During the baseline period, the person's glabrous blood flow fluctuated in a middle-upper range. This flow rate corresponds with a baseline blood pressure around 84. After the 18 minute mark, cooling was applied to the person's thermoregulatory control tissue, causing the glabrous blood flow rate to drop and causing a corresponding rise in blood pressure. At the 0.03 mark, the thermoregulatory control tissue was warmed. The warming greatly increased the glabrous blood flow, even beyond the baseline condition. This rise corresponds to a substantial drop in blood pressure over that same period of time.

Figure 8:
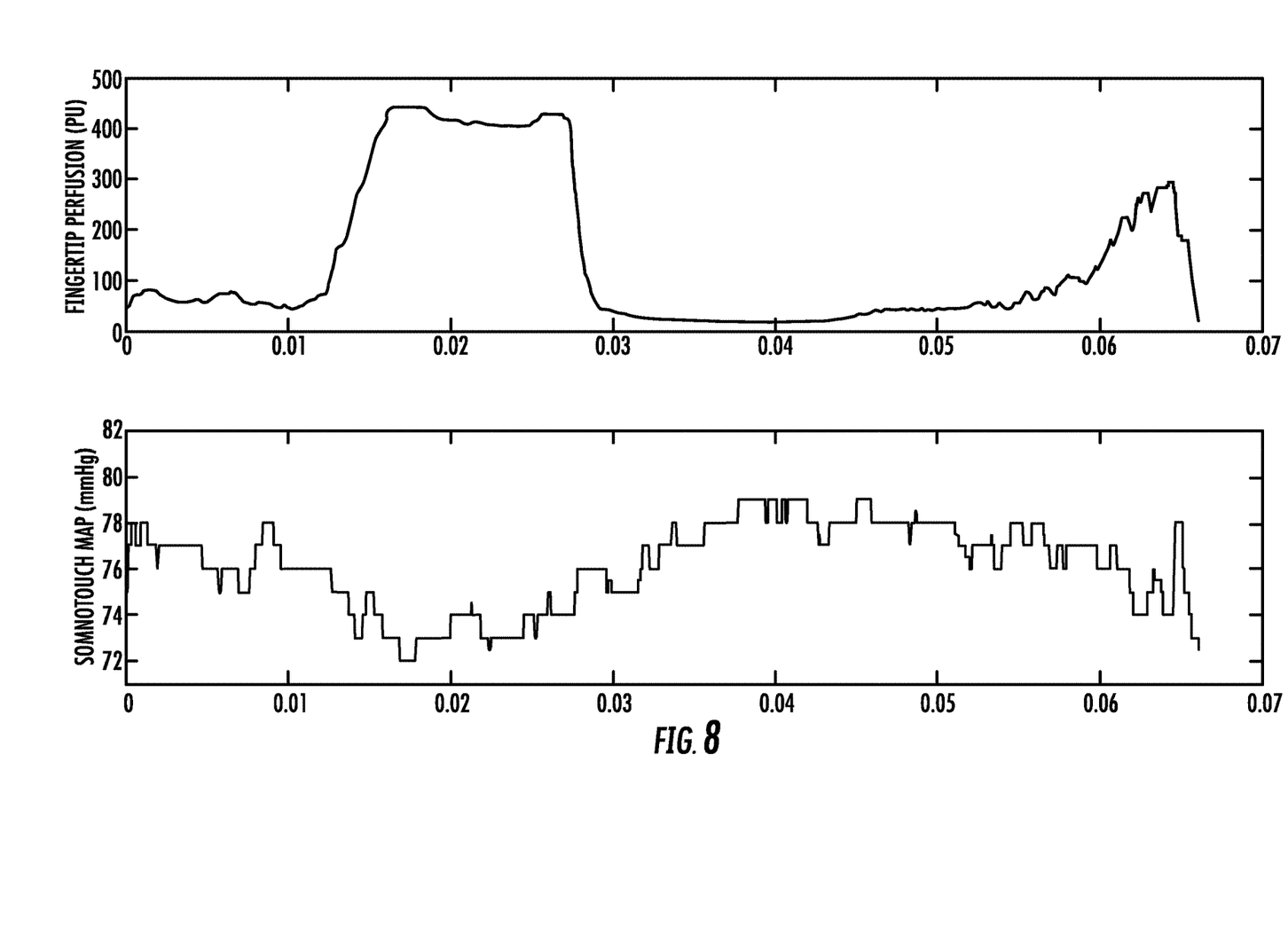
FIG. 8 is a pair of graphs showing data reflecting fingertip perfusion and mean arterial pressure over time in a subject.

FIG. 8 is a pair of graphs with similar measurements as those in FIGS. 5-7. After establishing a baseline, heating was applied at the 0.0125 mark. The heating raised the person's glabrous blood flow rate and caused a blood pressure drop. Subsequent cooling reduced the glabrous blood flow rate below that of the baseline and cased a rise in blood pressure, also beyond the baseline level.

Another exemplary study included ten healthy male subjects. The subjects were of the average age (+/−SD) of 21.1 (2.3), with a height of 174.5 (7.1) cm and an average weight of 77.0 (13.7) kg.

The study had a randomized crossover design. Each subject was randomly assigned to one of the two protocols on the first day of the experiment and underwent a second experiment, at least one week later, following the second protocol. Upon arrival, the subject spent the first thirty minutes passively acclimating to the room temperature. The next thirty minutes were spent instrumenting, during which time the subject donned a water-perfused suit (e.g., MED-ENG) over athletic shorts and a t-shirt. Each subject was then placed in the supine position. A two-hour experimental period included a thirty minute baseline period, thirty minutes of intervention 1, another 30 minute baseline period, and 30 minutes of intervention 2. The temperature of the water circulating through the suit was 33.5° C. during baseline, either 42.5° C. (H1) or 24.5° C. (C1) during intervention 1, 33.5° C. for the second baseline, and either 24.5° C. (C2) or 42.5° C. (H2), respectively, during intervention 2. The temperatures were chosen to induce vasoconstriction and vasodilation without triggering shivering or sweating. Each subject ran two trials in which the order of heating and cooling were inverted randomly.

Figure 9A:
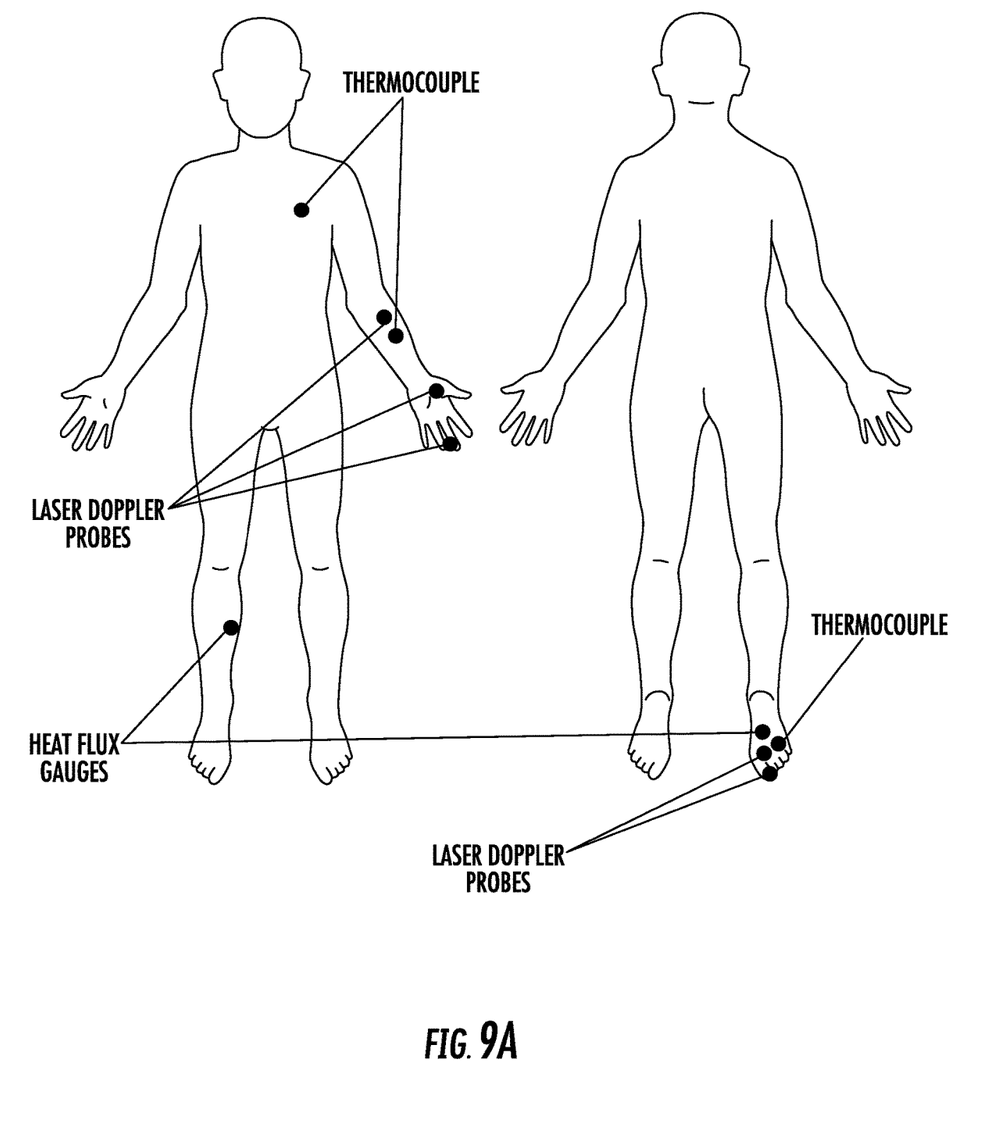
FIG. 9A is an instrumentation diagram for an exemplary study according to one implementation.

Core temperature was monitored with a thermocouple placed sublingually and stabilized by taping to the chin or cheek. Subjects were instructed not to expose the thermocouple to air. Surface instrumentation was applied in accordance with FIG. 9A. Multiple bead thermocouples and two heat flux gauges (e.g., from Concept Engineering) were used to monitor mean skin temperature and heat flux in both glabrous and nonglabrous regions, respectively. Laser Doppler flowmetry (LDF) probes (e.g., from Moor Instruments) were used to measure skin blood perfusion. LDF probes were applied to both glabrous and nonglabrous regions to investigate the differential effect of mean skin temperature manipulation on perfusion in AVA (glabrous region) and a capillary system (nonglabrous region). Blood pressure was measured using a blood pressure estimation device that estimates blood pressure based on measuring the pulse transit time and converting it to blood pressure values via a one point calibration (e.g., using a SOMNOtouch device from SOMNOmedics).

Data collected by the blood pressure estimation device was analyzed in MATLAB (version R2015a, MathWorks Inc.). The blood pressure and perfusion data were averaged for each baseline and intervention period, and the percent change from baseline was calculated using those means.

Figure 9B:
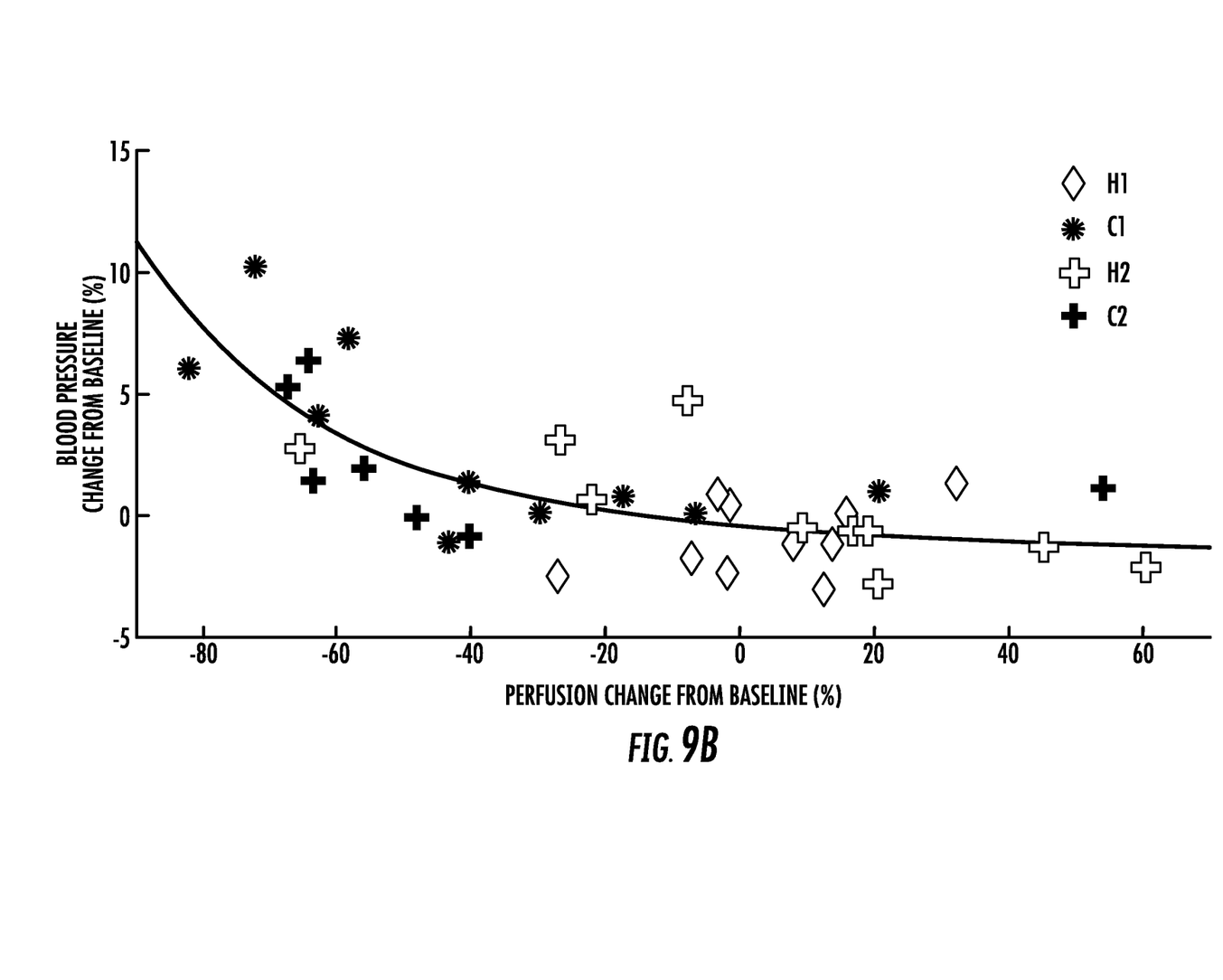
FIG. 9B is a graph showing the effect of change in skin perfusion on systemic blood pressure of ten subjects.

FIG. 9B shows the experimental data fitted exponentially to the following equation (R=0.7945):

$$SBP = ae^{bx} + ce^{dx}$$

wherein SBP is the percent change in systolic blood pressure, x is the percent change in fingertip perfusion, a is −0.8621, b is 0.006539, c is 0.4739, and d is −0.03565. FIG. 9B illustrates the effect of change in skin perfusion on the systemic blood pressure. The H1 and H2 data points represent the data from the first and second heating protocols, respectively, and the C1 and C2 data points represent the data from the first and second cooling protocols.

As shown in FIG. 9B, there is no significant difference regarding the order of intervention (p=0.51) or the percent changes in systolic and diastolic blood pressure (p=0.34). However, there is a significant difference between the 2 temperature groups ($p=1\times10^{-4}$).

Vasoconstriction and vasodilation were achieved in the absence of the discomfort of sweating and shivering. A relationship was developed between glabrous skin blood flow and both systolic and diastolic blood pressure. This coupling between the state of vasoconstriction and blood pressure is presumably related to alterations in peripheral vascular resistance.

FIGS. 5-9B provide real data supporting the correlation between increased glabrous blood flow and decreased blood pressure, as well as between decreased glabrous blood flow and increased blood pressure. These figures also show the rapid and direct effects of heating and cooling the peripheral thermoregulatory control tissue on glabrous blood flow.

While specific embodiments have been described in detail in the foregoing detailed description and illustrated in the accompanying drawings, it will be appreciated by those skilled in the art that various modifications and alternatives to those details could be developed in light of the overall teachings of the disclosure and the broad inventive concepts thereof. It is understood, therefore, that the scope of the present disclosure is not limited to the particular examples and implementations disclosed herein, but is intended to cover modifications within the spirit and scope thereof as defined by the appended claims and any and all equivalents thereof.

What is claimed is:

1. A system for modifying a person's blood pressure, comprising:
   a stimulating device to provide stimulation to at least a portion of the person's body, wherein said stimulation lowers the person's blood pressure by increasing or maintaining blood flow in the person's glabrous tissue;

a blood pressure monitor to monitor a blood pressure of the person;
a temperature sensor to determine a temperature of the person's glabrous tissue; and
a control system comprising a controller, the controller comprising a logic processor that is configured to:
receive a first blood pressure measurement from the blood pressure monitor,
compare the first blood pressure measurement to a predetermined threshold,
receive a temperature measurement of the person's glabrous tissue from the temperature sensor,
compare the received temperature measurement to stored data regarding a natural circadian cycle of temperature variation,
determine whether to modify the stimulation based on comparing the first blood pressure measurement to the predetermined threshold and comparing the received temperature measurement to the stored data regarding the natural circadian cycle of temperature variation, and
if a modification is needed, transmit a first instruction to adjust the stimulation, wherein the stimulating device adjusts the stimulation enough to lower the person's blood pressure below the predetermined threshold in response to the first instruction.

2. The system of claim 1, wherein the portion of the person's body corresponds to the person's peripheral thermoregulatory control tissue.

3. The system of claim 2, wherein the person's peripheral thermoregulatory control tissue comprises a cervical spinal region of the person.

4. The system of claim 2, wherein the person's peripheral thermoregulatory control tissue comprises a lumbar spinal region of the person.

5. The system of claim 1, wherein the stimulating device provides heating to the person's body such that the person's arteriovenous anastomoses (AVAs) are vasodilated.

6. The system of claim 5, wherein the heating is applied to the persons' peripheral thermoregulatory control tissue.

7. The system of claim 1, wherein the stimulating device provides cooling to the person's body such that the person's physiological temperature remains constant or is lowered.

8. The system of claim 1, wherein the stimulation comprises warming sufficient to lower the blood pressure of the person.

9. The system of claim 1, wherein said stimulating device is a climate-controlled bed.

10. The system of claim 9, wherein the climate-controlled bed comprises at least one climate zone.

11. The system of claim 10, wherein the climate-controlled bed includes an electric sourced heater and at least one conduit between the electric sourced heater and the climate zone, wherein fluid flowing through the conduit transfers heat to the climate zone from the electric sourced heater.

12. The system of claim 10, wherein the climate-controlled bed includes a thermoelectric sourced cooler and at least one conduit between the thermoelectric sourced cooler and the climate zone, wherein fluid flowing through the conduit transfers a cooling effect to the climate zone from the thermoelectric sourced cooler.

13. The system of claim 1, wherein the stimulating device includes a thermoelectric device.

14. The system of claim 13, wherein the thermoelectric device comprises an energy source, one or more conduits, and a fluid flowing through the conduits to transfer thermal energy between the energy source and at least one climate zone of the climate-controlled bed.

15. The system of claim 14, wherein the one or more conduits include at least one warming duct and at least one cooling duct, and the climate zones comprise a warming zone and a cooling zone, wherein the warming duct delivers warm air to the warming zone, and the cooling duct delivers cool air to the cooling zone.

16. The system of claim 13, wherein the control system further comprises a thermoelectric controller operably coupled to the controller, and wherein the thermoelectric controller is configured to:
receive the first instruction from the controller, and
control the thermoelectric device in response to the first instruction.

17. The system of claim 1, wherein the stimulating device provides said stimulation corresponding to the onset of sleep.

18. The system of claim 1, wherein the logic processor is further configured to:
receive a second blood pressure measurement from the blood pressure monitor, wherein the second blood pressure measurement is received after the stimulating device adjusts the stimulation in response to the first instruction,
compare the second blood pressure measurement to the predetermined threshold,
determine whether the person's blood pressure decreased below the predetermined threshold, and
transmit a second instruction to further adjust the stimulation, wherein the stimulating device further adjusts the adjusted stimulation in response to the second instruction.

19. The system of claim 1, wherein the stimulating device provides stimulation to at least a thoracic region of the person's body.

20. A method for modifying a person's blood pressure, comprising:
receiving a first blood pressure measurement of a person using a blood pressure monitor;
comparing the first blood pressure measurement to a predetermined threshold;
receiving a temperature measurement of the person's glabrous tissue from a temperature sensor,
comparing the received temperature measurement to stored data regarding a natural circadian cycle of temperature variation,
determining whether to modify a stimulation based on comparing the first blood pressure measurement to the predetermined threshold and comparing the received temperature measurement to the stored data regarding the natural circadian cycle of temperature variation; and
if a modification is needed, transmitting a first instruction to adjust a warming stimulus to at least a portion of the person's body enough to lower the person's blood pressure below the predetermined threshold by increasing or maintaining blood flow in the person's glabrous tissue, wherein the warming stimulus is adjusted in response to the first instruction.

21. The method of claim 20, wherein said warming stimulus causes the person's arteriovenous anastomoses (AVAs) to vasodilate.

22. The method of claim 20, wherein the portion of the person's body corresponds to the person's peripheral thermoregulatory control tissue.

23. The method of claim 22, wherein the person's peripheral thermoregulatory control tissue comprises a cervical spinal region of the person.

24. The method of claim 22, wherein the person's peripheral thermoregulatory control tissue comprises a lumbar spinal region of the person.

25. The method of claim 20, further comprising applying a cooling stimulus to the person's body such that the person's physiological temperature remains constant or is lowered.

26. The method of claim 20, further comprising:
receiving a second blood pressure measurement of the person using the blood pressure monitor, wherein the second blood pressure measurement is received after the warming stimulus is adjusted in response to the first instruction;
comparing the second blood pressure measurement to the predetermined threshold;
determining whether the person's blood pressure decreased below the predetermined threshold; and
if a modification is needed, transmitting a second instruction to further adjust the warming stimulus, wherein the warming stimulus is further adjusted in response to the second instruction.

27. The method of claim 20, wherein applying the warming stimulus corresponds to the onset of sleep.

28. The system of claim 20, wherein the warming stimulus is applied to at least a thoracic region of the person's body.

* * * * *